United States Patent
Goldmann et al.

(10) Patent No.: US 8,940,039 B2
(45) Date of Patent: Jan. 27, 2015

(54) REINFORCED VASCULAR PROSTHESIS WITH LONG-TERM ANTIMICROBIAL ACTION

(75) Inventors: Helmut Goldmann, Tuttlingen (DE); Dennis Langanke, Tuttlingen (DE)

(73) Assignee: Aesculap AG (DE)

( * ) Notice: Subject to any disclaimer, the term of this patent is extended or adjusted under 35 U.S.C. 154(b) by 974 days.

(21) Appl. No.: 12/238,788

(22) Filed: Sep. 26, 2008

(65) Prior Publication Data

US 2009/0082850 A1 Mar. 26, 2009

(30) Foreign Application Priority Data

Sep. 26, 2007 (DE) .................. 10 2007 047 246

(51) Int. Cl.
*A61F 2/06* (2013.01)
*A61L 27/50* (2006.01)
*A61L 27/54* (2006.01)
*A61F 2/07* (2013.01)

(52) U.S. Cl.
CPC ............... *A61L 27/507* (2013.01); *A61F 2/07* (2013.01); *A61F 2240/001* (2013.01); *A61L 27/54* (2013.01); *A61L 2300/104* (2013.01); *A61L 2300/404* (2013.01); *A61L 2300/606* (2013.01)
USPC ............. 623/1.22; 623/1.15; 623/1.46

(58) Field of Classification Search
USPC ............ 623/1.15, 1.42, 1.44–1.49, 1.52, 1.22
See application file for complete search history.

(56) References Cited

U.S. PATENT DOCUMENTS

| | | | |
|---|---|---|---|
| 3,479,670 A * | 11/1969 | Medell | 623/1.33 |
| 5,632,840 A | 5/1997 | Campbell | |
| 5,649,977 A | 7/1997 | Campbell | |
| 2005/0096737 A1 | 5/2005 | Shannon et al. | |
| 2005/0283224 A1 | 12/2005 | King | |
| 2006/0159720 A1* | 7/2006 | Lentz et al. | 424/425 |
| 2009/0068250 A1* | 3/2009 | Gravagna et al. | 424/426 |

FOREIGN PATENT DOCUMENTS

| | | |
|---|---|---|
| DE | 101 44 144 A1 | 7/2002 |
| DE | 103 23 676 A1 | 12/2004 |
| EP | 0 699 424 A2 | 3/1996 |
| WO | 96/04001 A1 | 2/1996 |
| WO | 96/40001 A1 | 12/1996 |
| WO | 97/33533 A1 | 9/1997 |
| WO | 99/09911 | 3/1999 |
| WO | 2007/001472 A2 | 1/2007 |

\* cited by examiner

*Primary Examiner* — Thomas J Sweet
*Assistant Examiner* — Matthew Schall
(74) *Attorney, Agent, or Firm* — DLA Piper LLP (US)

(57) ABSTRACT

A vascular prosthesis includes a prosthesis wall whose outer surface has at least one reinforcing means, the surface of the prosthesis wall and the surface of the at least one reinforcer being coated, at least in part, with an antimicrobial layer.

24 Claims, 2 Drawing Sheets

REINFORCED VASCULAR PROSTHESIS WITH LONG-TERM ANTIMICROBIAL ACTION

RELATED APPLICATION

This application claims priority of German Patent Application No. 102007047246.5, filed Sep. 26, 2007.

1. Technical Field

This disclosure relates to a vascular prosthesis with a reinforced outer surface and with long-term anti-microbial protection.

2. Background

In cases of implantation of vascular prostheses and other implants, infection is a complication feared by physicians and patients alike. The incidence of infection associated with an implant is approximately 0.5 to 5%. In the case of artificial vascular implants, risk factors include, for example, the subcutaneous positioning of vascular prostheses or their positioning in the inguinal region. The infections that occur may be so-called early or late infections. Early infections generally occur during a period of up to 4 months after the implantation. By contrast, late infections do not generally occur until a greater period of time has elapsed since the implantation. For example, there are clinical reports according to which infections of the aorta occurred after a period of 25 to 70 months. In the aorto-femoral position, the average time to the outbreak of infection is as much as 41 months.

Relevant pathogens include, in particular, *Staphylococcus aureus, Staphylococcus epidermidis*, methicillin-resistant *Staphylococcus aureus* (MRSA) and *Escherichia coli*. The infection arises usually as a result of contamination during surgery. However, it can also occur after surgery, particularly in cases where an infection suffered by the patient has not fully healed. Implants with long-term antimicrobial action are therefore becoming increasingly more important. A suitable implant in this respect is known from, for example, DE 103 23 676 A1.

In addition to long-term antimicrobial protection, the implants must also have a sufficient mechanical load-bearing capacity. This applies in particular to vascular prostheses which are implanted crossing a joint or as an extra-anatomical bypass. In this case, sufficient stability against kinking and compression is required above all. Vascular prostheses stable against kinking are known per se and are described in, for example, WO 9614001 A1, WO 97/33533 A1. EP 0 699 424 A2 and US 2005/0096737 A1.

It could therefore be helpful to provide a vascular prosthesis which provides antimicrobial protection, especially against possible late infections, and which at the same time has properties providing sufficient stability against kinking.

SUMMARY

We provide a vascular prosthesis comprising a prosthesis wall having an outer surface with at least one reinforcer having a surface, the surface of the prosthesis wall and the surface of the at least one reinforcer being coated, at least in part, with an antimicrobial layer.

We also provide a method of producing the vascular prosthesis, comprising:
 a) applying the at least one reinforcer to the outer surface of a vascular prosthesis to form a vascular prosthesis reinforced on its exterior; and
 b) coating the vascular prosthesis with an antimicrobial substance before and/or after application of the at least one reinforcer.

We further provide a method of for producing a vascular prosthesis, comprising:
 a) coating a vascular prosthesis with an antimicrobial substance; and
 b) applying the at least one reinforcer to the outer surface of the coated vascular prosthesis to form a coated vascular prosthesis reinforced on its exterior, the at least one reinforcer already being coated with the antimicrobial substance before application and/or the coated vascular prosthesis being coated again after application of the at least one reinforcer.

BRIEF DESCRIPTION OF THE DRAWINGS

Further features of our prostheses and methods will become evident from the following description in the form of examples in conjunction with the figures. Here, the individual features can each be realized singly or in combination with one another. The figures are hereby expressly made part of the content of the description.

In the figures.

DETAILED DESCRIPTION

Figure 1:
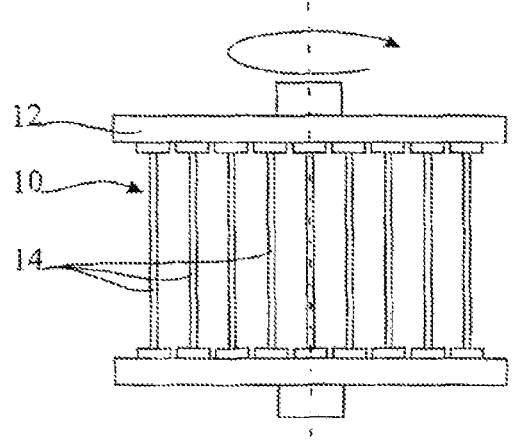
FIG. 1 shows the coating of vascular prostheses.

We provide a vascular prosthesis with a prosthesis wall whose outer surface has at least one reinforcing means, the surface of the prosthesis wall and the surface of the at least one reinforcing means being coated, at least in part, with an antimicrobial layer. If appropriate, the layer can comprise a plurality of antimicrobial layers.

The surface of the prosthesis wall having at least in part an antimicrobial layer is preferably the outer surface thereof, i.e., the surface of the prosthesis wall directed toward the outside of the prosthesis. Alternatively, or in combination, the surface of the reinforcing means can in particular be the outer surface thereof, i.e., the surface directed toward the outside of the prosthesis.

The at least one reinforcing means may be a reinforcing means that extends in a helical formation in the longitudinal direction of the vascular prosthesis.

Moreover, the at least one reinforcing means can be formed in an annular configuration on the outer surface of the prosthesis wall. In particular, the outer surface of the vascular prosthesis can have a plurality of annularly shaped reinforcing means. The annular reinforcing means can be arranged at regular or irregular intervals on the outer Surface of the prosthesis wall. The annular reinforcing means are preferably arranged at a constant spacing between one another. The number of the annularly formed reinforcing means can vary and is in particular dependent on the length of the prosthesis. The internal diameter of the annular reinforcing means is also preferably variable and depends in particular on the external diameter of the vascular prosthesis. In that construction, the annular reinforcing means are preferably present in the form of rings that each surround the outer surface of the vascular prosthesis at defined intervals.

It has surprisingly been found that a reinforced vascular prosthesis can be provided permanently with an antimicrobial coating even in the area of its reinforcing means, without compromising the mechanical properties that are conferred on the vascular prosthesis by virtue of its strengthening by the reinforcing means. We thus provide a vascular prosthesis in which both the prosthesis wall and also the at least one reinforcing means offer protection against infection. Consequently, the vascular prosthesis, in a particularly advantageous construction, can be provided with antimicrobial properties on the whole of its outer surface and in this way is able to prevent establishment of pathogens in the environment of the prosthesis, even over the long term. The at least one reinforcing means protects the vascular prosthesis against compressive loads and against kinking of the prosthesis.

The surface of the at least one reinforcing means may be completely coated with the antimicrobial layer. The outer surface of the prosthesis, in particular of the prosthesis wall, may also be completely coated with the layer. Preferably, at least one antimicrobial layer is located it the sites, in particular the helically extending sites, between the prosthesis wall and the at least one reinforcing means, in particular the helically extending reinforcing means. This is especially advantageous when performing anastomoses, where the prosthesis is usually sutured to a section of the natural vessel. For this purpose, a portion of the at least one reinforcing means is generally detached from the rest of the prosthesis, as a result of which the underlying areas of the outer surface of the prosthesis wall are exposed. In this case, complete protection against infection is ensured by the coating, of these outer surface areas. If so required, the vascular prosthesis can also be provided with an antimicrobial coating on the inner surface of the prosthesis wall. In this connection, reference is made to DE 103 23 676 A1, the subject matter of which is incorporated herein by reference.

In one possible construction, the sites mentioned in the previous paragraph, between the prosthesis wall and the at least one reinforcing means, can be free of an antimicrobial layer. Thus, only the outer surface of the at least one reinforcing means has an antimicrobial coating, i.e., the surface directed toward the outside of the vascular prosthesis.

The antimicrobial layer can have different layer thicknesses on the outer surface of the vascular prosthesis. The antimicrobial layer can in particular have different layer thicknesses on the outer surface of the prosthesis wall and/or on the surface of the at least one reinforcing means. This, the layer thickness of the antimicrobial layer on the prosthesis wall can be greater than on the at least one reinforcing, means, or vice versa. Preferably, the antimicrobial layer has identical layer thicknesses on the outer surface of the prosthesis wall and on the surface of the at least one reinforcing means.

In a further construction, the antimicrobial layer has a layer thickness of up to about 400 nm. The antimicrobial layer preferably has a layer thickness of between about 40 nm and about 200 nm, in particular of between about 80 nm and about 160 nm.

The at least one reinforcing means is preferably secured permanently on the outer surface of the prosthesis wall. Preferably, the at least one reinforcing means is affixed to the outer surface of the prosthesis wall, for example, with the aid of a hot-melt adhesive suitable for this purpose.

The at least one reinforcing means may be a filament-like structure. The at least one reinforcing means can be a monofilament or multifilament. The at least one reinforcing means is preferably a monofilament. Provision can also be made for the at least one reinforcing means to be in the form of a thread, yarn or wire. For example, the thread can be a hot-melt thread.

The thread, in particular the hot-melt thread call further be enveloped with a hot-melt adhesive. In other words, the at least one reinforcing means is preferably a hot-melt adhesive sheathed thread. The hot-melt adhesive can in particular be based on a copolymer with polybutylene. A band-shaped configuration of the at least one reinforcing means is also possible according to the invention.

The at least one reinforcing means is preferably made of a plastic. The plastic can be resorbable or preferably non-resorbable. The plastic material can be a polyester or a polyolefin, preferably a polypropylene. In a particularly preferred construction, the at least one reinforcing means is a polypropylene thread.

Possible materials for producing the prosthesis wall are the polymers customarily used in vascular prostheses, such as, for example, in particular polyester, polytetra-fluoroethylene (PTFE), polyurethane and, in special cases, also polyamides. The use of polyester, in particular polyethylene terephthalate and/or polytetra-fluoroethylene, in particular expanded polytetra-fluoroethylene (ePTFE), is particularly preferred.

The prosthesis wall preferably has a wall thickness from about 0.1 to about 1 mm, in particular from about 0.4 to about 0.6 mm. The prosthesis wall and preferably also the antimicrobial layer may be porous.

In case of a vascular prosthesis designed as a knitted vascular prosthesis, the prosthesis can be obtained by warp knitting as a single tricot fabric for example. With the single tricot knitting technique, also named single tricot weave, merely one guide bar is used for knitting. Furthermore, the vascular prosthesis can be formed by warp knitting in a double tricot weave. Generally, this knitting procedure uses two guide bars. The vascular prosthesis can be obtained by a combination of weave types and knitting techniques. Examples of such combined knitting techniques include weaves like tricot-satin, tricot-pillar stitch, pillar stitch/weft, and combinations including filet techniques.

Fundamentally, the vascular prosthesis can be formed of monofilament threads or multifilament threads, in particular multifilament yarns. Generally, the threads have a circular cross section. The vascular prosthesis can be composed of a number from about 10 to about 70 filaments, in particular from about 35 to about 45 filaments. Furthermore, the vascular prosthesis can have a yarn count from about 30 to about 200 dtex, preferably from about 40 to about 60 dtex.

The prosthesis can have a radial tear resistance $\geq 5$ N/mm, in particular from about 10 to about 25 N/mm.

The vascular prosthesis is preferably a textile vascular prosthesis. The vascular prosthesis can in principle be in the form of a knitted fabric, braided fabric, woven fabric or non woven fabric. The vascular prosthesis is particularly preferably a knitted vascular prosthesis. Provision can also be made for the vascular prosthesis to be a double-velour prosthesis.

The vascular prosthesis may be unpleated.

The antimicrobial layer generally comprises an antimicrobial substance. Combinations of antimicrobial active substances may also be employed.

In principle, the antimicrobial layer on the surface of the prosthesis wall can have other antimicrobial substances than on the surface of the at least one reinforcing means, or vice versa. The antimicrobial layer on the surface of the prosthesis wall and the one on the surface of the at least one reinforcing means preferably have the same antimicrobial substance or antimicrobial substances. Particularly preferred is that the antimicrobial active layer has a proportion of antimicrobial active substance from about 0.05 to about 1.0% by weights in particular from about 0.10 to about 0.40% by weight, based on the total weight of the vascular prosthesis. Generally, an impregnation coating will also contribute to the total weight of the vascular prosthesis, as will be discussed in detail below.

Antimicrobial substances that can be used are in particular antimicrobial metals and/or their salts. The antimicrobial metals are in particular platinum, iridium, gold, silver and/or copper. Silver is preferred. The metal salts can in particular be metal oxides. The salts that can be used are preferably sparingly soluble. The salt is particularly preferably a sparingly soluble silver salt. The antimicrobial layer is preferably a metal layer, in particular a layer of metallic silver. A metal layer, in particular a silver layer, can be generated by means of vapor-deposition methods known per se, for example, the IBAD (ion-beam assisted deposition) method. It is particularly preferable if the metal atoms of the metal layer are embossed into the outer surfaces of the prosthesis wall and/or of the at least one reinforcing means. This can be done in particular by bombarding these outer surfaces with, for example, argon ions during vapor deposition.

The antimicrobial layer of the vascular prosthesis is preferably a closed layer. However, in the case of a porous vascular prosthesis wall, this does not mean that its pores are closed by the layer. Rather, the antimicrobial layer can adapt to the surface structure of the vascular prosthesis, such that the pores retain their original shape and size.

A primer layer call be present between the outer surface of the prosthesis wall and the antimicrobial layer. The primer layer can be composed, in particular, of titanium, niobium and/or tantalum.

The vascular prosthesis may be impregnated, the impregnation preferably involving a sealing impregnation or coating. The impregnation is preferably present in the form of an impregnation layer. Biocompatible materials may be considered as the impregnation materials. For example, the vascular prosthesis can be impregnated with biological materials, in particular with collagen gelatin and/or albumin. The biological materials are preferably of xenogenic origin, in particular of bovine, porcine and/or equine origin. The impregnation materials are preferably crosslinked. Suitable compounds for this purpose are in particular di-functional, tri-functional, tetra-functional or in general oligo-functional compounds, for example, diisocyanates or glutaraldehyde. Other suitable impregnation materials are synthetic polymers that are degradable or resorbable in vivo, in particular copolymers. In addition to at least partially water-soluble polymers, such as polyvinyl alcohol and/or carboxymethylcellulose, the main candidates here are polymers and copolymers based on hydroxycarboxylic acids. The vascular prosthesis is preferably impregnated with polymers or copolymers based on glycolide, lactide, $\epsilon$-caprolactone. trimethylene carbonate and/or p-dioxanone. The desired duration of resorption can be set by suitable choice of the polymers. This can be 4 months in particular, preferably 40 days. Such a time period is especially favorable since, depending on the nature of the vascular prosthesis, the impregnating action is no longer necessary after this period on account of the connective tissue that grows in. The vascular prosthesis preferably has a sealing impregnation that encloses the antimicrobial layer.

We further provide methods for producing the vascular prosthesis, comprising the steps of:
  a) applying the at least one reinforcing means, in particular an elongate reinforcing means, to the outer surface of a vascular prosthesis to form a vascular prosthesis reinforced on its outside, in particular reinforced in a helical structure; and
  b) coating the vascular prosthesis with an antimicrobial substance before and/or after the application of the at least one reinforcing means, in particular of the elongate reinforcing means.

The at least one reinforcing means can be coated with an antimicrobial substance independently of the vascular prosthesis, i.e., before application to the outer surface of the vascular prosthesis.

Application of the at least one reinforcing means to the outer Surface of the vascular prosthesis is performed preferably during spiraling of tile vascular prosthesis.

To apply the at least one reinforcing means onto the outer surface of the vascular prosthesis, a polymer thread can be spun on and expediently wound onto the vascular prosthesis in a still moist state.

The production method may comprise the steps of:
  a) coating, a vascular prosthesis with an antimicrobial substances and
  b) applying the at least one reinforcing means to the outer surface of the coated vascular prosthesis to form a coated vascular prosthesis reinforced on its outside, the at least one reinforcing means already being coated with the antimicrobial substance before application and/or the coated vascular prosthesis being coated after the application of the at least one reinforcing means.

The at least one reinforcing means may be applied to the outer surface of the vascular prosthesis by means of an adhesive, preferably a hot-melt adhesive. The at least one reinforcing means can also itself be formed by a hot-melt adhesive.

Coating the vascular prosthesis with an antimicrobial substance may be carried out by metal deposition. The metal deposition is usually done in a vacuum chamber, the metal atoms preferably being applied in ionized form to the vascular prosthesis. Such metal deposition can be carried out, for example, with the aid of the IBAD (ion-beam assisted deposition) method.

The vascular prosthesis may be coated by appropriate impregnation materials. In that context, reference is made to the previous description in its entirety. Generally, the vascular prosthesis will be sterilized subsequent to its production, preferably using ethylene oxide. Preferably, an ethylene oxide sterilization is performed in case the at least one reinforcing means is a polypropylene thread.

Example 1

Antimicrobial Coating of Vascular Prostheses (FIG. 1)

Prostheses 10 made of polyester (polyethylene terephthalate) or ePTFE are clamped in a rotatable clamping device 12 such that they hang freely alongside one another as a bundle of parallel tubes 14 with spaces between them. The clamping device 12 is placed in a vacuum chamber suitable for carrying out the IBAD method, wherein a silver vapor deposition of the vascular prostheses 10 is carried out with simultaneous bombardment with argon ions. The coating process is continued until a thickness of the silver layer of ca. 130 nm is achieved on the outside of the vascular prostheses 10 or of the fibers lying there. If so desired, a primer can first be formed by vapor deposition with other metals, for example, with titanium and/or palladium.

Example 2

Figure 2A:
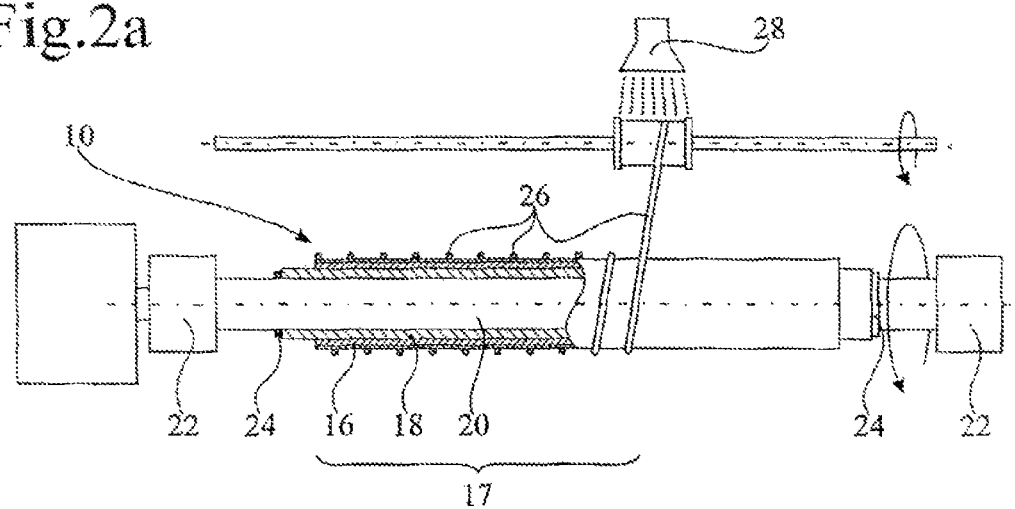
FIGS. 2*a* and 2*b* show the helically shaped reinforcing of an antimicrobially coated vascular prosthesis.
Figure 2B:
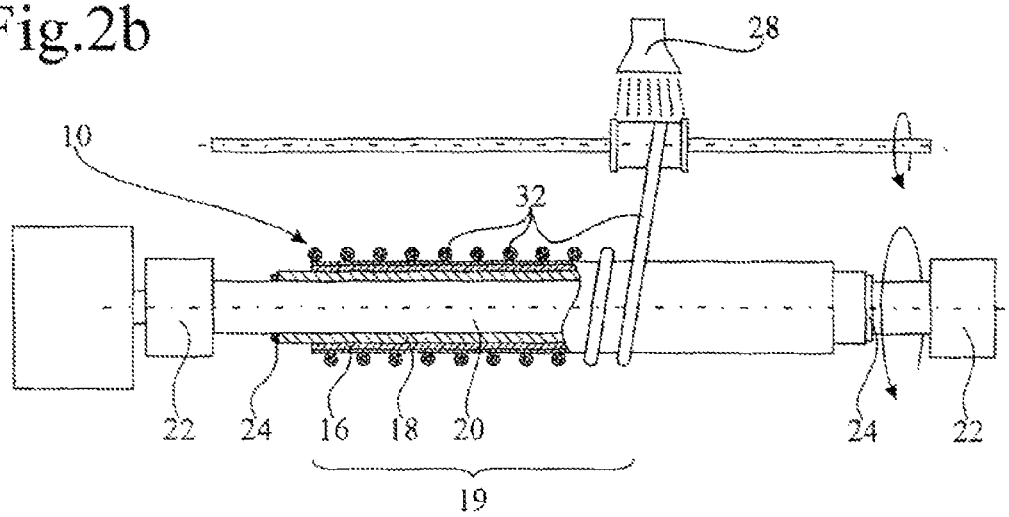

Helical Reinforcing of the Antimicrobially Coated Vascular Prosthesis (FIGS. 2a and 2b)

Silver-coated vascular prosthesis blanks 16 made of polyester (polyethyelene terephthalate) or ePTFE are drawn onto a tube 18 made of polyethylene, for example, with an internal diameter of 4.2 mm and an external diameter of 6.0 mm. This unit is pushed onto a steel rod 20, for example, with an external diameter of 4 mm. The steel rod 20 is clamped at both ends by drill chucks 22 and fixed at both ends with cable binders 24. A silver-free hot-melt thread 26, for example, a polypropylene thread enveloped with a hot-melt adhesive, is guided and braked (e.g. 5 newton) by means of a hysteresis brake. The control unit is set to the usable length, for example, 1020 mm. Thereafter, the spindle is set to 90 rpm (revolutions per minute). The hot-air unit 28 is set to 180° C. A time delay of ca. 2 minutes as set-up time ensures that the temperature is constant. The operating time for application of the hot-melt thread 26 amounts to ca. 6 minutes (pitch: 4 mm). After a cooling period of ca. 5 minutes, the polyethylene tube 18 (PE tube) with the helically reinforced vascular prosthesis 17 is drawn off from the steel wire 20. The vascular prosthesis 17 is withdrawn from the polyethylene tube 18 by stretching, for example, with gripper forceps.

The helically reinforced, coated vascular prosthesis 17 is then subjected to renewed silver coating according to Example 1. The vascular prosthesis thus coated is removed from the clamping device and then impregnated in the usual way with a resorbable material 30 at least on its outer face (see FIG. 4). Impregnation of the vascular prosthesis 36 can be carried out, for example, with gelatin, which is at least partially crosslinked with glutaraldehyde or a suitable diisocyanate. Biologically active substances can be introduced into the coating solution in order to develop a biological activity during the subsequent resorption of the layer.

Instead of the silver-free hot-melt thread 26 used in Example 2, it is also possible in principle to use a hot-melt thread 32 already coated with silver, in which case the hot-melt thread 32 is, for example, a polypropylene thread which has first been coated with silver and thereafter with a hot-melt adhesive. The helically reinforced and coated vascular prosthesis 19 thus obtained can be subjected to further silver vapor deposition, if appropriate, for example, if still exposed adhesive is also to be provided with an antimicrobial coating.

Example 3

Figure 3:
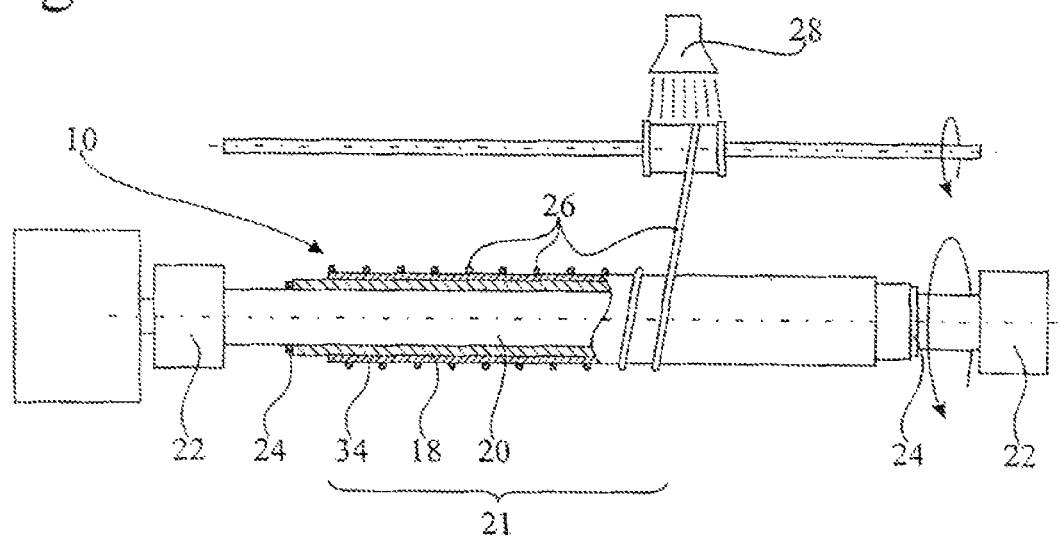
FIG. 3 shows the helical reinforcing of an uncoated vascular prosthesis.

Helical Reinforcing of an Uncoated Vascular Prosthesis (FIG. 3)

Uncoated vascular prosthesis blanks 34 made of polyester (polyethylene terephthalate) or ePTFE are drawn onto a tube 18 made of polyethylene, for example, with an internal diameter of 4.2 mm and an external diameter of 6.0 mm. This unit is pushed onto a steel rod 20, for example, with an external diameter of 4 mm. The steel rod 20 is clamped at both ends by drill chucks 22 and fixed at both ends with cable binders 24. A silver-free hot-melt thread 26, or if appropriate a silver-coated hot-melt thread 32 (cf. FIG. 2*b*), is guided and braked (e.g. 5 newton) by means of a hysteresis brake. The control unit is set to the usable length, for example, 1020 mm. Thereafter, the spindle is set to 90 rpm (revolutions per minute). The hot-air unit 28 is set to 180° C. A time delay of ca. 2 minutes as set-up time ensures that the temperature is constant. The operating time for application of the hot-melt thread 26 amounts to ca. 6 minutes (pitch: 4 mm). After a cooling period of ca. 5 minutes, the polyethylene tube 18 (PE tube) with the helically reinforced uncoated vascular prosthesis 21 is drawn off from the steel rod 20. The vascular prosthesis 21 is withdrawal from the polyethylene tube 18 by stretching, for example, with gripper forceps.

Figure 4:
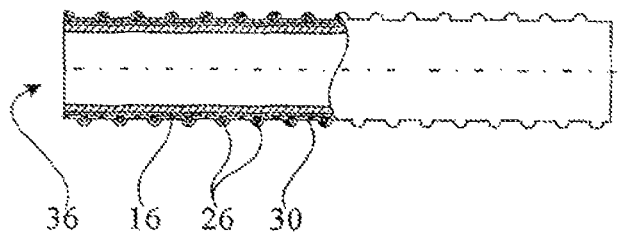
FIG. 4 shows a helically reinforced, antimicrobially coated and impregnated vascular prosthesis.

The helically reinforced vascular prosthesis 21 is then provided with an antimicrobial coating in accordance with Example 1. The vascular prosthesis thus coated is removed from the clamping device and, as has been described under Example 2, is impregnated with gelatin (FIG. 4).

Figure 5:
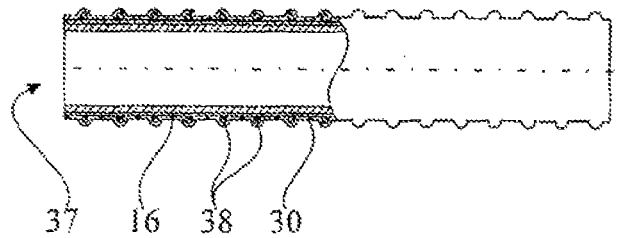
FIG. 5 shows an annularly reinforced, antimicrobially coated and impregnated vascular prosthesis.

FIG. 5 is a schematic representation of an annularly reinforced, silver-coated vascular prosthesis 37 which is impregnated on its outer face with a resorbable material 30, for example, crosslinked gelatin. The reinforcing means 38 present in the form of individual rings strengthen the vascular prosthesis at regular intervals on the outer surface of the prosthesis wall.

Example 4

Product Characteristics of one Construction of the Vascular Prosthesis

Prosthesis base:

| Prostesis base: | |
|---|---|
| Polyester: | knitted |
| Weave: | tricot-tricot (countercurrent) |
| Yarn count: | 50 dtex |
| Number of filaments: | 40 |
| Yarn cross section: | circular |
| Orientation line (black) | |
| Water permeability: | 1500 ml/cm$^2$ * min |
| Spiral: | |
| Material: | monofilament polypropylene, sheathed by a polybutylene rich hot-melt adhesive |
| Cross section: | 0.76 mm |
| Amount of coating: | 64% |
| Linear tear strength: | 130 N |
| Distance of spiral: | 3.9 mm |
| Adhesive strength of spiral: | 7.5 N |
| Prostesis characteristics: | |
| Wall thcikness: | 0.51 mm |
| Radial tear strength: | 12.5 N |
| Coating/Impregnation: | |
| Coating thickness silver: | 125 nm |
| Silver content: | 0.28% by weight |
| Gelatine content: | 11.5% by weight |
| Glycerol content: | 12.7% by weight |

The invention claimed is:

1. A vascular prosthesis comprising a prosthesis wall having an outer surface with one reinforcer having a surface, the surface of the prosthesis wall and the surface of the one reinforcer being coated, at least in part, with an antimicrobial layer, wherein the one reinforcer is a hot-melt adhesive enveloped thread extending in a helical formation in a longitudinal direction of tile vascular prosthesis.

2. The vascular prosthesis as claimed in claim 1, wherein the at least one reinforcer is annularly configured.

3. The vascular prosthesis as claimed in claim 1, wherein the surface of the at least one reinforcer is completely coated.

4. The vascular prosthesis as claimed in claim 1, wherein the outer surface of the prosthesis wall is completely coated.

5. The vascular prosthesis as claimed in claim 1, wherein the at least one antimicrobial layer is located at sites between the prosthesis wall and the at least one reinforcer.

6. The vascular prosthesis as claimed in claim 1, wherein the antimicrobial layer on the outer surface of the vascular prosthesis has different layer thicknesses.

7. The vascular prosthesis as claimed in claim 1, wherein the antimicrobial layer has different layer thicknesses on the outer surface of the prosthesis wall and on the surface of the at least one reinforcer.

8. The vascular prosthesis as claimed in claim 1, wherein the antimicrobial layer has identical layer thicknesses on the outer surface of the prosthesis wall and on the surface of the at least one reinforcer.

9. The vascular prosthesis as claimed in claim 1, wherein the antimicrobial layer has a layer thickness of up to about 400 nm.

10. The vascular prosthesis as claimed in claim 1 wherein the antimicrobial layer has a layer thickness or between about 40 nm and about 200 nm.

11. The vascular prosthesis as claimed in claim 1, wherein the at least one reinforcer is adhesively affixed to the outer surface of the prosthesis wall.

12. The vascular prosthesis as claimed in claim 1, wherein the at least one reinforcer is a monofilament.

13. The vascular prosthesis as claimed in claim 1, wherein the at least one reinforcer is made of polypropylene.

14. The vascular prosthesis as claimed in claim 1, wherein the prosthesis wall and the antimicrobial layer are porous.

15. The vascular prosthesis as claimed in claim 1 wherein the prosthesis is a knitted vascular prosthesis.

16. The vascular prosthesis as claimed in claim 1 wherein the prosthesis is a double-velour prosthesis.

17. The Vascular prosthesis as claimed in claim 1 wherein the prosthesis is unpleated.

18. The vascular prosthesis as claimed in claim 1, wherein the antimicrobial layer is a layer of metallic silver.

19. The vascular prosthesis as claimed in claim 1, wherein the antimicrobial layer has a proportion of antimicrobial active substance from about 0.05 to about 1.0% by weight, based on the total weight of the vascular prosthesis.

20. The vascular prosthesis as claimed in claim 1, wherein the antimicrobial layer contains a sparing soluble silver salt.

21. The vascular prosthesis as claimed in claim 1, further comprising a primer layer between the outer surface of the prosthesis wall and the antimicrobial layer.

22. The vascular prosthesis as claimed in claim 1, where in the prosthesis is at least partly impregnated with crosslinked gelatin.

23. The vascular prosthesis as claimed in claim 22, wherein the impregnation encloses the antimicrobial layer.

24. A vascular prosthesis comprising a prosthesis wall having an outer surface with one reinforcer having a surface, the surface of the prosthesis wall and the surface of the one reinforcer being coated, at least in part, with an antimicrobial layer, wherein the one reinforcer is a hot-melt adhesive sheathed thread extending in a helical formation in a longitudinal direction of the vascular prosthesis, wherein the hot-melt adhesive is a copolymer of polybutylene.

* * * * *